Figure 1:
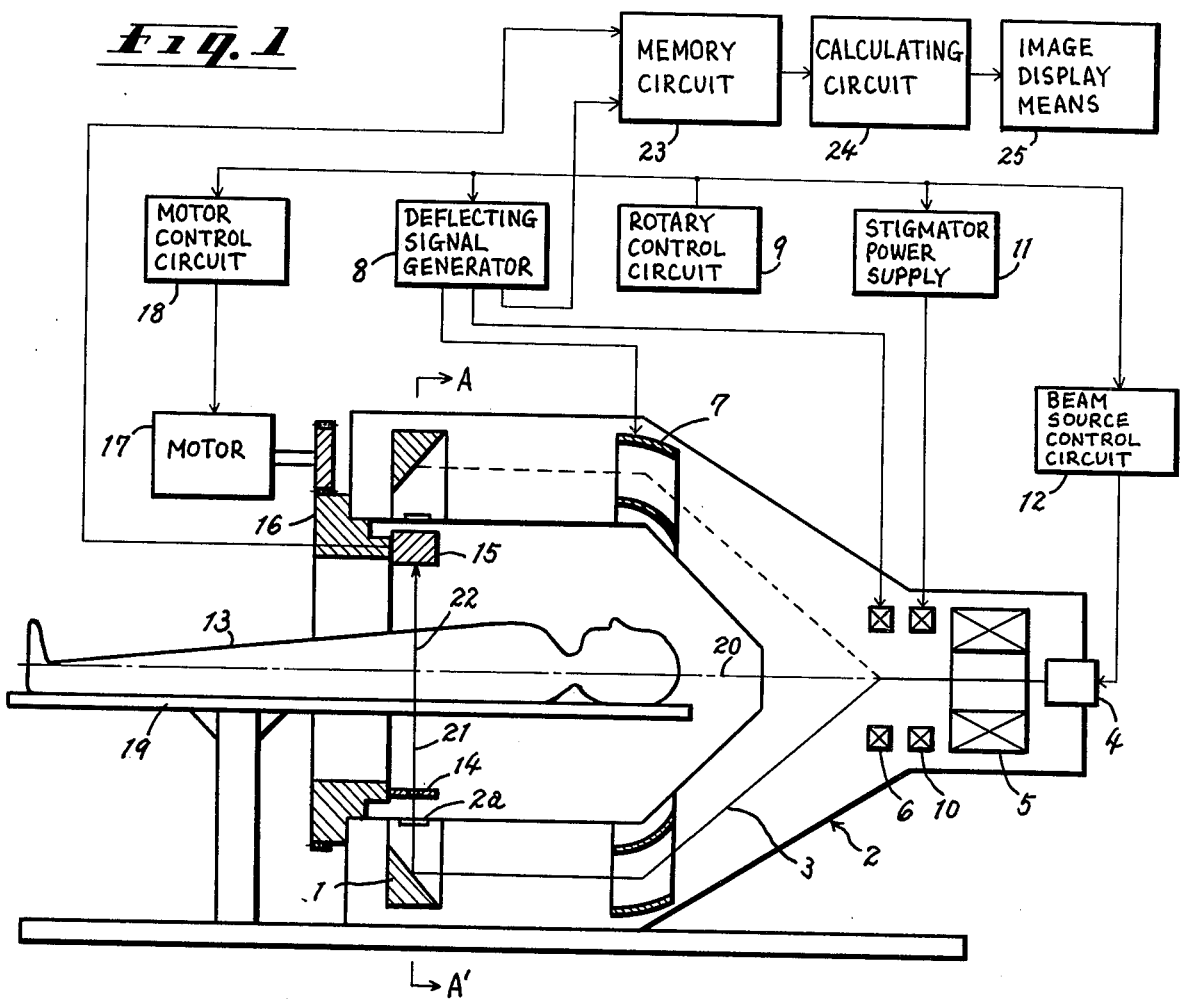

United States Patent [19]

Watanabe

[11] 4,135,095
[45] Jan. 16, 1979

[54] APPARATUS FOR OBTAINING AN X-RAY IMAGE

[75] Inventor: Eiji Watanabe, Tokyo, Japan

[73] Assignee: Nihon Denshi Kabushiki Kaisha, Tokyo, Japan

[21] Appl. No.: 770,659

[22] Filed: Feb. 22, 1977

[30] Foreign Application Priority Data

Feb. 28, 1976 [JP] Japan .................................. 51-21712
Mar. 5, 1976 [JP] Japan .................................. 51-23995
Mar. 11, 1976 [JP] Japan .................................. 51-26376

[51] Int. Cl.² ............................................. A61B 6/02
[52] U.S. Cl. .................................. 250/445 T; 250/360
[58] Field of Search .................... 250/360, 366, 445 T

[56] References Cited

U.S. PATENT DOCUMENTS

| 3,106,640 | 10/1963 | Oldendorf | 250/445 T |
| 4,002,917 | 1/1977 | Mayo | 250/445 T |
| 4,010,370 | 3/1977 | LeMay | 250/445 T |
| 4,031,395 | 6/1977 | LeMay | 250/445 T |

Primary Examiner—Alfred E. Smith
Assistant Examiner—T. N. Grigsby
Attorney, Agent, or Firm—Webb, Burden, Robinson & Webb

[57] ABSTRACT

A computed tomography apparatus in which a fan-shaped X-ray beam is caused to pass through a section of an object, enabling absorption detection on the opposite side of the object by a detector comprising a plurality of discrete detector elements. An electron beam generating the X-ray beam by impacting upon a target is caused to rotate over the target.

10 Claims, 9 Drawing Figures

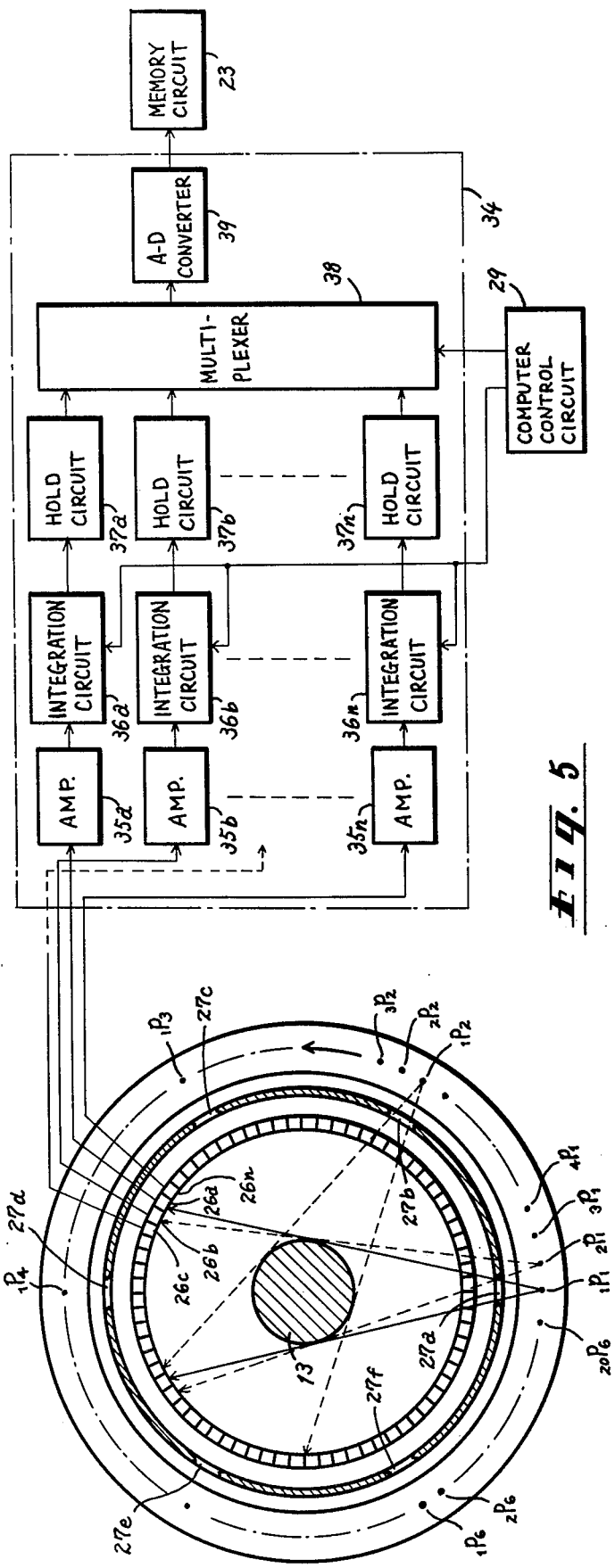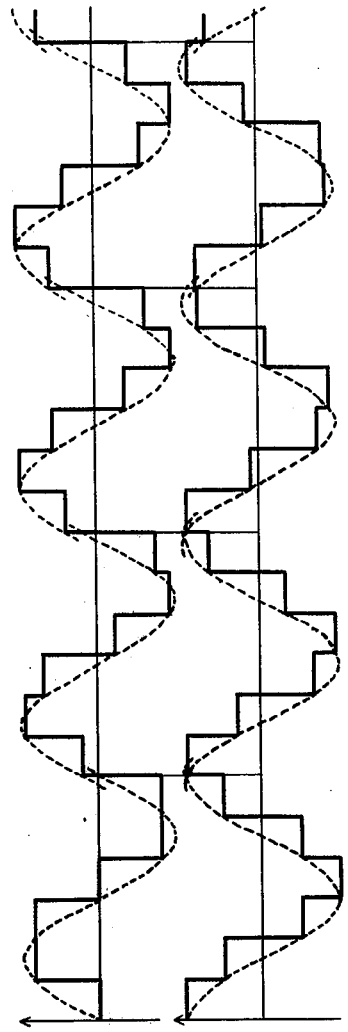
fig. 5
fig. 6(a)
fig. 6(b)

APPARATUS FOR OBTAINING AN X-RAY IMAGE

This invention relates to an apparatus for observing in three dimensions the organic structure of an animate object (for example, a human being, hereinafter referred to as the patient) by means of X-ray irradiation.

A method of examining a patient by X-ray irradiation known as computed tomography was recently developed to obtain more information than hitherto possible with a conventional X-ray projection image. In this method, the X-ray generating source is rotated around the longitudinal axis of the patient so that X-rays from said source irradiate and pass through a selected cross-sectional slice plane of the patient. The X-rays thus transmitted are then detected by a means equipped with a plurality of small detecting elements. Thereby, each hypothetical micro matrix area on said selected cross-sectional slice plane is irradiated many times in as many directions by an X-ray beam and the resultant information is detected. The outputs of the detecting elements are then fed into a computer which computes the X-ray absorption coefficient at each micro matrix area based on the detected data and the position data corresponding to the direction of the irradiating X-ray beam path. The X-ray image of the slice plane is then obtained by displaying in two dimensions the values corresponding to the X-ray absorption coefficients of the respective matrix areas.

This method, however, has certain disadvantages in that the apparatus embodying said method is very complicated; moreover, in order to obtain information on one X-ray image in one slice plane, a relatively long measuring time is required.

Accordingly, it is an advantage of this invention to reduce the measuring time for obtaining one X-ray image of one slice plane of an object.

Yet another advantage of this invention is to simplify or remove the mechanical measuring procedure for carrying out the computer tomography method.

These advantages are achieved by using an X-ray generating apparatus incorporating apparatus for deflecting and rotating the electron beam over the surface of an annular or partially annular target thereby changing the direction of the X-ray beam irradiating the object.

Figures 2, 3:
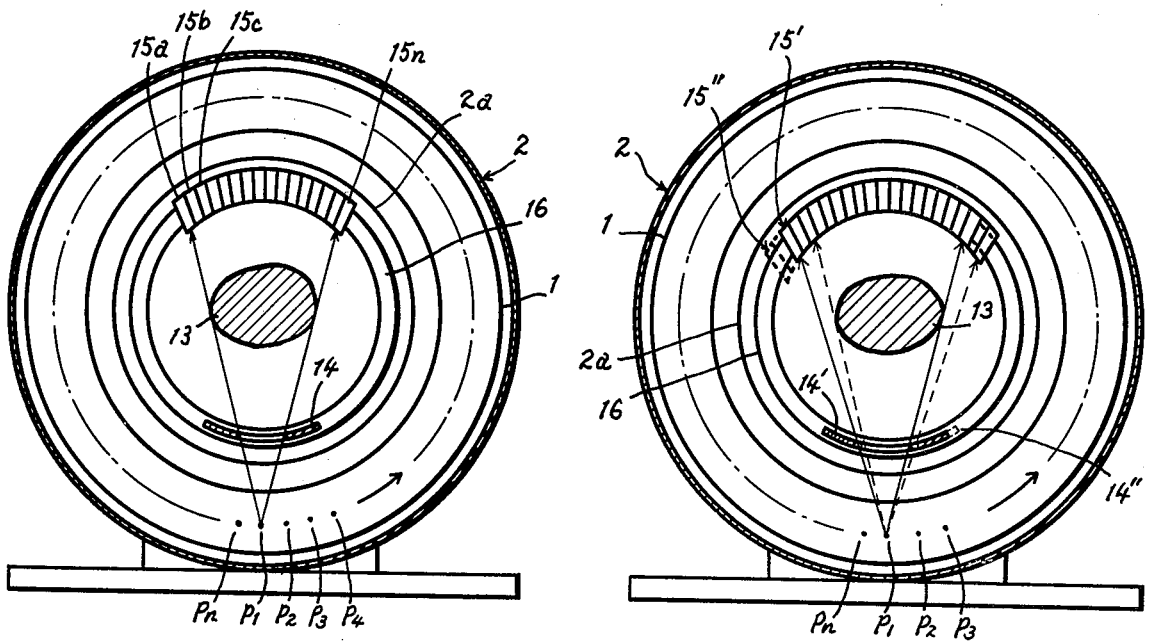
Figure 4:
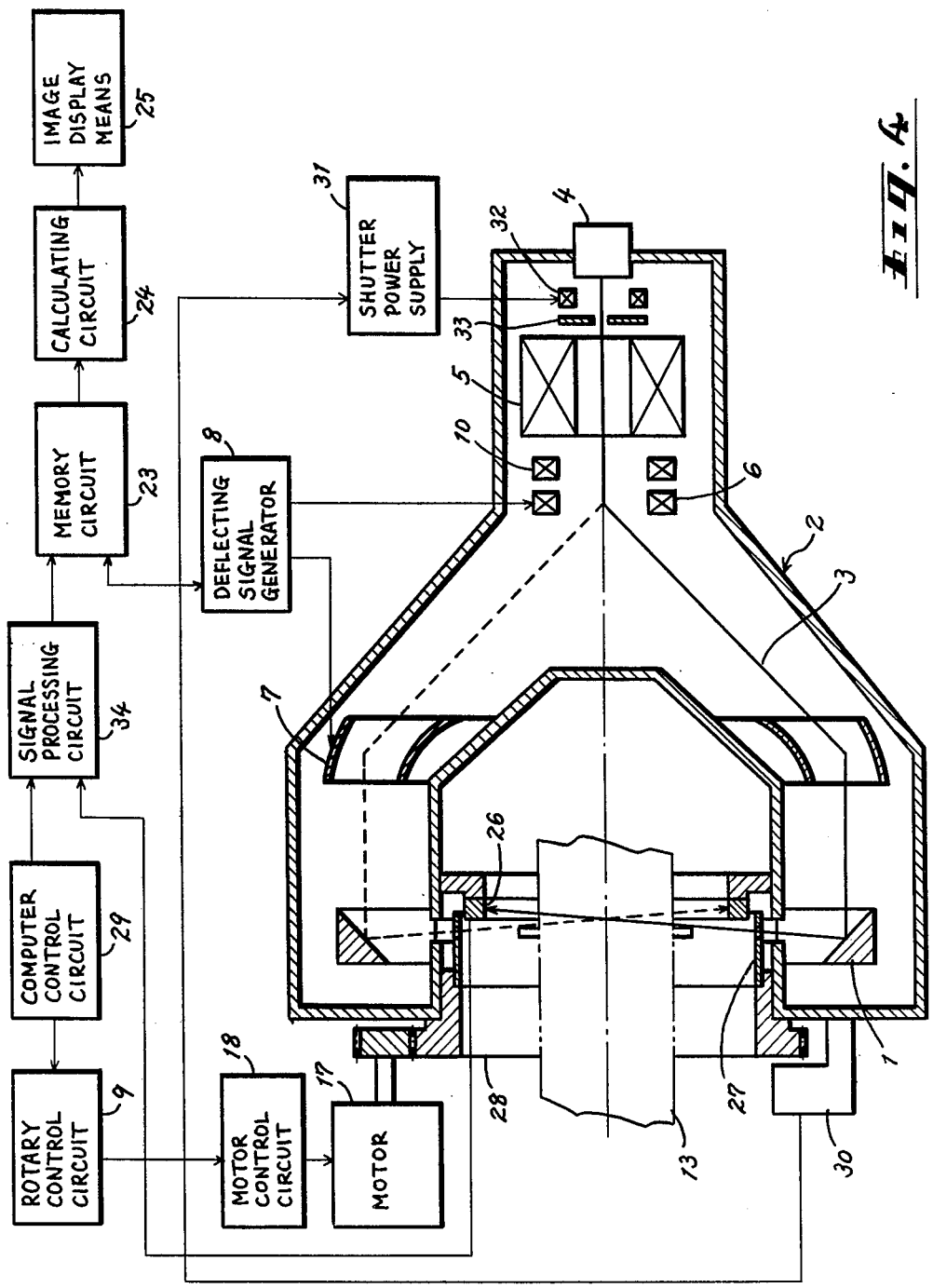
Figure 7:
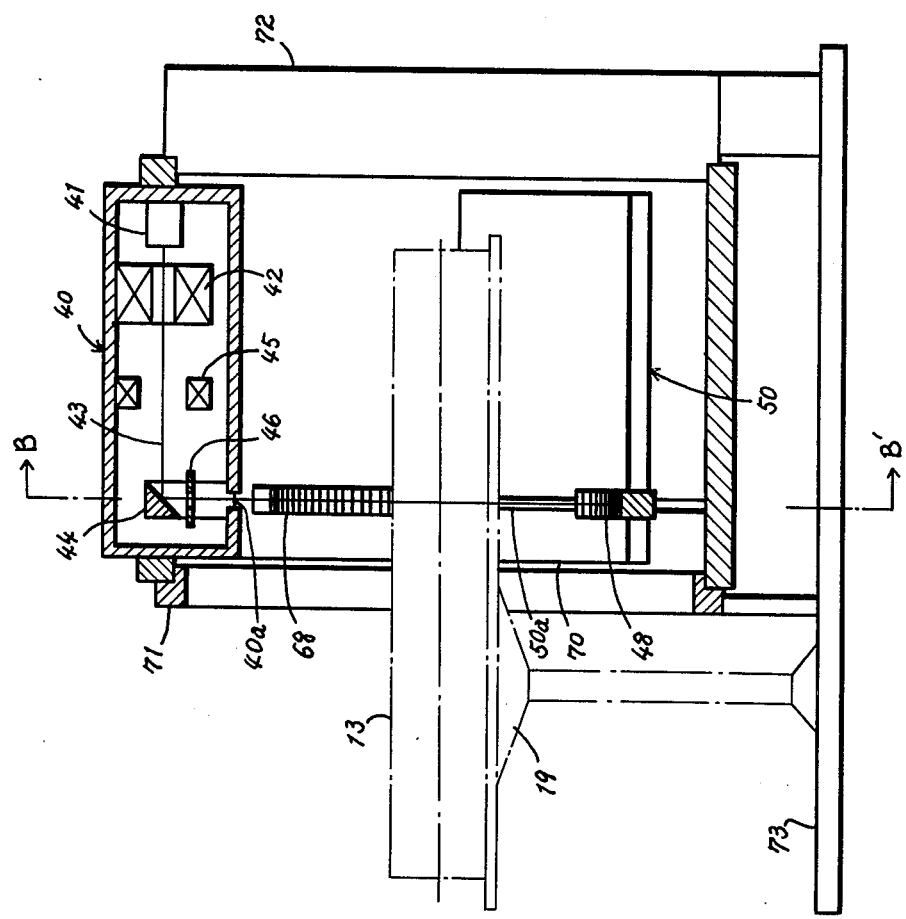
Figure 8:
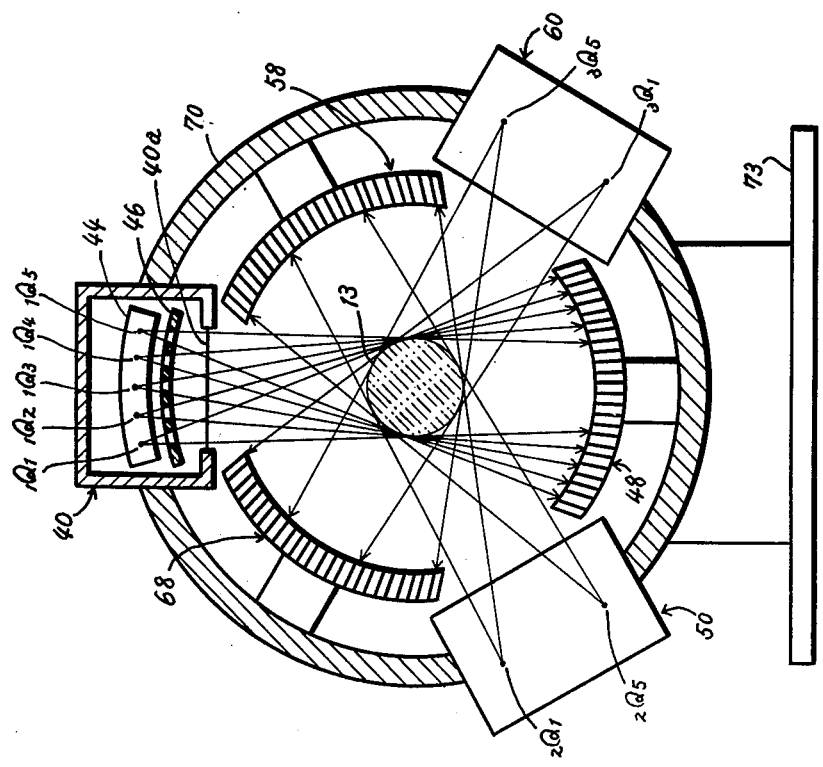

Other features and advantages of this invention will become more readily apparent by reading the following description in conjunction with the accompanying drawings of which:

FIG. 1 is a schematic drawing showing one embodiment according to this invention, FIGS. 2 and 3 are cross-sectional views of the FIG. 1 embodiment, FIGS. 4 and 5 are schematic drawings showing another embodiment of this invention, FIGS. 6a and 6b are diagrams showing the signals used in the FIGS. 4 and 5 embodiment, and FIGS. 7 and 8 are schematic drawings showing yet another embodiment according to this invention.

Briefly, according to this invention, a computed tomograph comprises an X-ray generating column in which a finely focused electron beam irradiates an annular target, resultant upon which, said target emits a fan-shaped X-ray beam whose take-off direction is varied by shifting said finely focused electron beam over said annular target. An X-ray detecting means, located antipodally with respect to said target, detects the X-rays passed through a thin slice plane of an animated object (for example, a human being) located between said target and said detecting means. A rotary signal is applied to a deflecting means so as to rotate the X-ray beam generating point around the center axis of the target, the output signals from said deflecting and detecting means being memorized by a memory circuit. A calculating circuit then calculates the X-ray absorption coefficient at each micro matrix area on said slice plane of the object and supplies the respective outputs to an image display means so as to display an X-ray image of said slice plane of the object.

In the FIG. 1, an annular target 1 is located at one end of a bell-shaped vacuum column 2. An electron beam 3 generated by an electron beam generating source 4 is focused by a condenser lens 5 and deflected by deflecting means 6 and 7, so as to irradiate the surface of the annular target 1 with a fine diameter or a beam having a small elliptical cross-sectional. The deflecting means 6 and 7, the latter of which is composed of two co-axial ring-shaped electrodes, are supplied with signals from a deflecting signal generator 8 so as to move the beam continuously or digitally along the circle on said target 1. The deflecting signal generator 8 is in turn controlled by a rotary control circuit 9. A stigmator 10 and its power supply 11 are also controlled by the rotary control circuit 9. The stigmator 10 is used to compensate for any distortion in the shape of the cross-sectional plane of the electron beam at the target surface caused by deflecting means 6 and 7. The rotary control circuit 9 also controls a beam source control circuit 12 which in turn controls the electron beam generating source 4. By so doing (i.e., by controlling the electron beam generating source 4), it becomes possible to irradiate the target only during the time an object (for example, a patient) 13 is being examined and thereby prevent the temperature of the target from exceeding the critical value.

A beam guide 14 and a detector 15 comprising a plurality of detecting elements are antipodally supported on a ring 16, said ring 16 being rotated by a motor 17. The rotation of the ring 16 is controlled by the rotary control circuit 9 via a motor control circuit 18. The height of an X-ray table 19 upon which the patient 13 reclines, is adjustable so that the longitudinal axis of the patient more or less coincides with the center axis 20 of the annular member 16 and with the center beam generated by the electron beam generating source 4. The position of said annular member 16 and the location of the beam irradiating point on the target are controlled by the rotary control circuit 9 so that a fan-shaped X-ray beam 21 passes through a cross-sectional slice plane 22 of the patient 13 via an X-ray window 2a and the beam guide 14 slit, prior to being detected by the detector 15.

FIG. 2 shows a sectional view of FIG. 1 taken through A—A'. As shown by the figure, the electron beam irradiating point is varied intermittently, as shown by P1, P2, P3 .... Pn, in synchronism with the annular member 16 which is shifted stepwise. For this purpose, two deflecting signals are applied to the deflecting means 6, said signals being formed by dividing the sine-wave and cosinewave signals stepwise. Detecting elements 15a, 15b, ... 15n are equipped with collimators to prevent the detection of scattered X-rays.

In the embodiment shown in FIG. 1, the fan-shaped X-ray beam 21 irradiates and passes through a cross-sectional slice plane 22 of the patient 13 from many different directions at three degree intervals, prior to being detected and measured by the respective detecting elements 15a, 15b, ... 15n. The X-ray beam intensity varies in accordance with the X-ray absorption at each transmitted X-ray path within the patient's body. The detector 15 output signals are then memorized by a memory circuit 23 together with a signal which is simultaneously applied to said memory circuit from the deflecting signal generator 8, said signal corresponding to the position of the X-ray generating point on the target surface. The information memorized by the memory circuit 23 is then fed into a calculating circuit 24 which calculates the X-ray absorption coefficient of each hypothetical matrix area on the cross-sectional slice plane 22 of the patient 13. Finally, the calculated signals are fed into an image display means 25 which displays an X-ray image of the slice plane 22.

In the embodiment as described above, the rotation of the annular member 16 and that of the X-ray generating point on the target surface are carried out intermittently. However, it is possible to continuously rotate the annular member 16 as shown in FIG. 3 so as to more accurately control the mechanical drive of said member. In this case, the annular member 16 is continuously rotated at a constant speed during the time the electron beam irradiating point momentarily stops at P1, P2 ... Pn. However, by so doing, since the beam guide 14' and the detector 15' are shifted to positions 14" and 15", it is necessary to lengthen the slit and window by increasing the number of detecting elements, in order to nullify the influence of said shift.

A partially annular target may also be used in lieu of a fully annular target. In this case, if the rotation of the annular member 16 is restricted to within 300° by structural obstructions, an X-ray tomographic image having almost the same image quality as in the case of the embodiment according to FIG. 1 is obtainable.

FIG. 4 shows another embodiment of the subject invention in which the X-ray detecting method is different from that in the FIG. 1 embodiment. In FIG. 4, constituent parts having numbers corresponding to those in FIG. 1 are identical. In this embodiment, an annular X-ray detector 26 equipped with a plurality of tiny detecting elements 26a, 26b, ... 26n is fixed to the column 2. An X-ray beam guide 27 having six slits 27a, 27b ... 27f spaced at regular intervals is supported by an annular member 28 which is rotated by the motor 17. The motor 17 is in turn controlled by a computer control circuit 29 via the rotary control circuit 9 and the motor control circuit 18. The position of the beam guide 27 slit is detected by a rotation detecting means 30 which also detects the rotation of the annular member 28 optically. The output signal from the rotation detecting means 30, which is used for positioning the X-ray generating point on the target, is supplied to the deflecting signal generator 8 and to shutter power supply 31. The shutter power supply 31 in turn supplies signals to a deflecting means 32 so as to prevent the electron beam 3 from passing through baffle slit 33 during the time when the patient 13 is not being irradiated by the X-ray beam. In effect then, the function of the deflecting means 32 and the slit 33 is identical to that of the beam source control circuit 12 in the embodiment explained with reference to FIG. 1. The output signal from the rotation detecting means 30 is also supplied to the memory circuit 23 together with the output signal from a signal processing circuit 34 which serves to process the output signal from the X-ray detector 26 in accordance with the control signal from the computer control circuit 29. In this embodiment, the direction of the fan-shaped X-ray beam is slightly inclined with respect to the cross-sectional plane perpendicular to the center axis of the annular member 28 so as to enable the X-ray beam to be detected by the annular detector 24 without being obstructed by the beam guide 27.

FIG. 5 shows a cross-sectional view of the FIG. 4 embodiment. The irradiating point of the electron beam is determined by applying the control signals shown in FIG. 6 (a) and (b) to electron beam deflecting means 6 and 7, said control signals being derived by approximating the sine and cosine waves stepwise at regular intervals of time and by slightly shifting the phase of the sine and cosine waves at the end of each cycle. As a result, the irradiating point of the electron beam on the target is shifted from $_1P_1 \rightarrow {}_1P_2 \rightarrow {}_1P_3 \rightarrow \ldots \rightarrow {}_1P_6$ in sequence and then from $_2P_1 \rightarrow {}_2P_2 \rightarrow {}_2P_3 \rightarrow \ldots \rightarrow {}_2P_6$ in sequence and so on until twenty sequences are completed. In this case, the beam guide rotates stepwise, for example 3° for each rotation of the electron beam on the target, so as to bring the spaced slits 27a, 27b ... 27f into line with the center axis 20 of the ring 16 and the initial irradiating point of the subsequent series. That is to say, by the time the electron beam has completed 20 target rotations, the beam guide has rotated 60° (3° × 20). Such being the case, the position of the beam guide slits are the same as it was when the measurement commenced. Thus, one complete measuring sequence comprises 120 (2 × 60) X-ray irradiations each having a different direction.

If the beam guide rotates at, say, 1800 r.p.m., one full measurement takes less than 1/30 sec.

If it is required to rotate the beam guide continuously instead of stepwise as described above, it will be necessary to lengthen the beam guide slits for reasons as given in the description under FIG. 3.

Increasing the number of beam guide slits and changing the rotation angle of the beam guide per one rotation of the electron beam on the target, according to requirements, may be accommodated. For example, by making the beam guide stationary during measurement, a very low resolution X-ray tomographic image can be obtained within a very short time.

The respective outputs of the X-ray detecting elements 26a, 26b ... 26n are amplified by amplifiers 35a, 35b ... 35n, integrated by integration circuits 36a, 36b ... 36n, and fed into a multiplexer 38 via hold circuits 37a, 37b ... 37n. The multiplexer 38 then selects the required holder circuit outputs and passes them into the memory circuit 23 via an A-D converter 39.

The computer control circuit 29 sends a reset signal to integration circuits 36a, 36b ... 36n and a signal to the multiplexer 38 each time the irradiating point of the electron beam on the target changes. In this way, the required measurement data is accumulated and calculated prior to being displayed as a tomograph image of a cross-sectional plane of the patient.

FIG. 7 shows yet another embodiment of this invention and FIG. 8 shows a cross-sectional view of said embodiment taken through B—B'. In the figure, 40, 50 and 60 are identical X-ray beam generating columns symmetrically mounted on a cylindrical chamber 73. The cylindrical chamber 70 is rotatable supported by members 71 and 72 which are mounted on a base plate 72. Each column is equipped with an electron beam source 41, 51 or 61 (51 and 61 are not shown) for generating an electron beam 43, 53 or 63 (53 and 63 are not shown), a condenser lens 42, 52 or 62 (52 and 62 are not shown), for converging said respective electron beams on a target 44, 54 or 64 (54 and 64 are not shown), and a deflecting means 45, 55 or 65 (55 and 65 are not shown) for rotatably deflecting said respective electron beams on said respective targets, so as to describe a circle whose center axis accords with the center axis of the cylindrical chamber 70, as shown by $_1Q_1$, $_1Q_2$, $_1Q_3$, $_1Q_4$, $_1Q_5$, $_2Q_1$, ... $_2Q_5$, $_3Q_1$, ... $_3Q_5$. X-ray beam guides 46, 56 and 66 (56 and 66 are not shown) are each equipped with five slits. Accordingly, fan-shaped X-rays 47a, 47b and 47c emitted from targets 44, 54 and 64 concomitant with electron beam impingement, are directed towards and pass through the patient 13 reclining on the X-ray table 19 via X-ray window 40a, 50a, 60a (50a is not shown).

Detectors 48, 58 and 68 arranged antipodally with respect to targets 44, 54 and 64 and equipped with many tiny X-ray detecting elements detect the respective X-ray beams passed through the patient 13. The outputs of said detectors are then processed in the same way as in the case of the FIG. 5 embodiment. After which, the processed signals are memorized by a memory circuit (not shown) together with the cylindrical chamber 70 rotational position signals and the signals applied to deflecting means 45, 55 and 65. Finally, the output of said memory circuit is fed into a display means so as to display a tomographic image of an optional cross-sectional slice plane of the patient 13.

In this embodiment, the three fan-shaped X-ray beams simultaneously irradiate the patient 13 in three different directions, and are respectively detected by three X-ray detecting means. Accordingly, irradiation data relevant to nine irradiating directions is obtainable by deflecting the electron beam without rotating the cylindrical chamber 70. Thus, by additionally rotating said chamber an abundance of data relevant to many irradiating directions can be obtained in short order. As a result, it becomes possible to execute a measuring sequence so rapidly that it can be synchronized with variation signals of very short duration. It therefore becomes easy to obtain tomographic images of vital anatomical organs, such as the heart, which change shape by dilating and contracting in continuous sequence, simply by controlling the apparatus embodying this invention in accordance with the signals monitoring said organ variation. It is also possible to increase or decrease the number of X-ray beam generation columns and/or the number of X-ray beam guide slits as required.

Having thus described my invention with the detail and particularity as required by the Patent Laws, what is desired protected by Letters Patent is set forth in the following claims.

1. An apparatus for obtaining a two dimensional image of an X-ray absorption distribution on a cross-sectional plane of an object comprising:
   a. a source for generating an electron beam,
   b. a target, in part annular, for generating a fan-shaped X-ray beam, the angle of the fan being sufficient to cover the entire region of interest in said object, said target being fixed with respect to said object,
   c. means for focusing said electron beam on said target,
   d. means for rotating said electron beam around the target so as to irradiate said target intermittently in a predetermined fashion,
   e. means for detecting and measuring the intensity of portions of each X-ray beam passed through the object comprising a plurality of detecting elements,
   f. means for memorizing the output of said detecting means along with the corresponding output signals from the rotating means,
   g. means for calculating the absorption value at each micro matrix area on said cross-sectional plane from the data memorized in the memory (f), and
   h. means for displaying said respective calculated absorption values.

2. An apparatus according to claim 1 in which said electron beam source, said target, said focusing means, and said rotating means are housed in a bell-shaped vacuum column.

3. An apparatus according to claim 1 in which said rotating means comprises a plurality of deflecting stages, at least one of said deflecting stages comprising a pair of co-axial ring-shaped electrodes.

4. An apparatus according to claim 1 in which said detecting means is at least partially annular and is fixed.

5. An apparatus according to claim 1 including a beam guide having at least one slit for directing the fan-shaped X-ray beam.

6. An apparatus according to claim 5 in which said beam guide, and said detecting means are rotated by a mechanical rotating means in synchronism with said rotating means.

7. An apparatus according to claim 5 in which said beam guide is rotated by a mechanical rotating means in synchronism with said rotating means and said detecting means being fixed.

8. An apparatus according to claim 5 in which said beam guide and said detecting means are both fixed.

9. An apparatus according to claim 5 in which said electron beam is rotated on the target surface by said rotating means faster than said beam guide rotates mechanically.

10. An apparatus for obtaining a two dimensional image of the X-ray absorption distribution on a cross-sectional plane of an object comprising:
    a. a plurality of fan-shaped X-ray beam generating columns, each of which comprise
       i. a source for generating an electron beam,
       ii. a target for generating an X-ray beam,
       iii. means for focusing said electron beam on said target,
       iv. means for deflecting said electron beam on said target, and
       v. a beam guide having slits for directing the fan-shaped X-ray beam onto the object,
    b. a chamber onto which said fan-shaped X-ray beam generating columns are symmetrically mounted so that the fan-shaped X-ray beams are directed towards the object positioned along the center axis of said chamber,
    c. means mounted on said chamber between said fan-shaped X-ray beam generating columns means for detecting and measuring the intensity of portions of each X-ray beam passed through the object,
    d. a rotating means for rotating said chamber on its center axis,
    e. means for memorizing the outputs of said detecting means together with the corresponding signals applied to the deflecting means housed in the X-ray beam generating column and the signal from said rotating means,
    f. means for calculating the absorption value at each micro matrix area on said cross-sectional plane from the data memorized in the memory, and
    g. means for displaying in two dimensions said respective calculated absorption values.

* * * * *